United States Patent [19]

Gates

[11] 4,064,250
[45] Dec. 20, 1977

[54] INSECTICIDAL BENZODIOXOL-4-YL CARBAMATES AND INTERMEDIATES THEREOF

[75] Inventor: Peter Stuart Gates, Cambridge, England

[73] Assignee: Fisons Limited, England

[21] Appl. No.: 677,845

[22] Filed: Apr. 16, 1976

[30] Foreign Application Priority Data

May 2, 1975 United Kingdom ............... 18341/75

[51] Int. Cl.$^2$ ........................ A01N 9/28; C07D 317/46
[52] U.S. Cl. ............................... 424/282; 260/340.5 R
[58] Field of Search .................. 260/340.5 R; 424/282

[56] References Cited

U.S. PATENT DOCUMENTS 3,948,952   4/1976   Gates et al. ...................... 260/340.5

Primary Examiner—Dolph H. Torrence
Attorney, Agent, or Firm—Wenderoth, Lind & Ponack

[57] ABSTRACT

There are provided benzodioxol-4-yl carbamates of the formula:

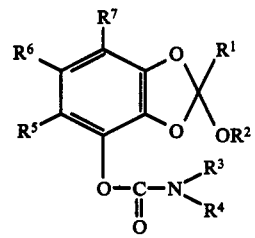

(I)

where $R^1$ represents H, alkyl or phenyl; $R^2$ represents alkyl; $R^3$ represents H, alkyl, alkenyl, alkynyl, alkanoyl or benzoyl; $R^4$ represents alkyl, alkenyl or alkynyl; and $R^5$, $R^6$ and $R^7$, which may be the same or different, each represent H, halogen, or alkyl.

The compounds are insecticidal.

12 Claims, No Drawings

INSECTICIDAL BENZODIOXOL-4-YL CARBAMATES AND INTERMEDIATES THEREOF

This invention concerns benzodioxolyl carbamates, processes for their preparation, and insecticidal compositions containing them.

In one aspect this invention provides the benzodioxol-4-yl carbamates of the general formula:

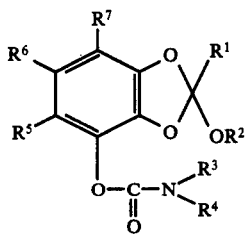

(I)

wherein: $R^1$ represents hydrogen, an alkyl group preferably of 1 to 6 carbon atoms such as methyl, ethyl, n-propyl or iso-propyl, which may be unsubstituted or substituted for example by halogen (such as chlorine or bromine), by alkylthio (such as ethylthio) or by alkoxy (such as methoxy or ethoxy), a phenyl group which may be unsubstituted or substituted for example by halogen (such as chlorine or bromine), by alkoxy (such as methoxy or ethoxy) or by alkyl (such as methyl or ethyl), or a group $-OR^2$ where $R^2$ is as defined hereinafter; $R^2$ represents an alkyl group preferably of 1 to 6 carbon atoms (such as methyl, ethyl or n-propyl), which may be unsubstituted or substituted for example by halogen (such as chlorine or bromine) or by alkoxy (such as methoxy or ethoxy); $R^3$ represents hydrogen or an alkyl, alkenyl or alkynyl group preferably of not more than 4 carbon atoms such as methyl, ethyl, allyl, propargyl or butynyl, which may be unsubstituted or substituted for example by halogen (such as chlorine, bromine or iodine) or by alkoxy (such as methoxy or ethoxy), an alkanoyl group preferably of 2 to 10 carbon atoms such as acetyl, propionyl or hexanoyl, or benzoyl; $R^4$ represents an alkyl, alkenyl or alkynyl group preferably of not more than 4 carbon atoms such as methyl, ethyl, allyl, propargyl or butynyl, which may be unsubstituted or substituted for example by halogen (such as chlorine, bromine or iodine) or by alkoxy (such as methoxy or ethoxy); and $R^5$, $R^6$ and $R^7$, which may be the same or different, each represent hydrogen, halogen (such as chlorine or bromine), or an unsubstituted alkyl group preferably of 1 to 4 carbon atoms such as methyl or ethyl.

$R^1$ preferably represents hydrogen or a substituted or unsubstituted alkyl group.

When $R^1$ represents a substituted alkyl or phenyl group, it is preferably a chloromethyl, ethylthiomethyl, 2-chloroethyl, 4-chlorophenyl, 3,4-dichlorophenyl, 3-methoxypropyl, or a tolyl group.

When $R^1$ represents a group $-OR^2$, it is preferably a methoxy, ethoxy or 4-methoxyphenoxy group.

When $R^2$ represents a substituted alkyl group, it is preferably a 2-chloroethyl or 3-methoxypropyl group.

When $R^3$ represents a substituted alkyl, alkenyl or alkynyl group, it is preferably a 2-chloroethyl, 3-methoxypropyl, 3-chloroallyl, 2,3-dichloroallyl, 3-iodopropargyl or 4-chlorobutynyl group.

When $R^4$ represents a substituted alkyl, alkenyl or alkynyl group, it is preferably a 2-chloroethyl, 3-methoxypropyl, 3-chloroallyl, 2,3-dichloroallyl, 3-iodopropargyl or 4-chlorobutynyl group.

$R^5$, $R^6$ and $R^7$ are all preferably hydrogen.

Specific preferred compounds according to the present invention include:
2-methoxy-1,3-benzodioxol-4-yl N-methylcarbamate,
2-methoxy-2-methyl-1,3-benzodioxol-4-yl N-methylcarbamate,
2-methoxy-2-ethyl-1,3-benzodioxol-4-yl N-methylcarbamate,
2-methoxy-2-n-propyl-1,3-benzodioxol-4-yl N-methylcarbamate,
2-methoxy-2-isopropyl-1,3-benzodioxol-4-yl N-methylcarbamate,
2-methoxy-2-chloromethyl-1,3-benzodioxol-4-yl N-methylcarbamate,
2-methoxy-2-phenyl-1,3-benzodioxol-4-yl N-methylcarbamate,
2,2-dimethoxy-1,3-benzodioxol-4-yl N-methylcarbamate,
2-ethoxy-1,3-benzodioxol-4N-methylcarbamate,
2-ethoxy-2-methyl-1,3-benzodioxol-4-yl N-methylcarbamate,
2-ethoxy-2-ethyl-1,3-benzodioxol-4-yl N-methylcarbamate,
2-ethoxy-2-n-propyl-1,3-benzodioxol-4-yl N-methylcarbamate,
2-ethoxy-2-isopropyl-1,3-benzodioxol-4-yl N-methylcarbamate,
2-ethoxy-2-chloromethyl-1,3-benzodioxol-4-yl N-methylcarbamate,
2-ethoxy-2-ethylthiomethyl-1,3-benzodioxol-4-yl N-methylcarbamate,
2-propoxy-2-ethyl-1,3-benzodioxol-4-yl N-methylcarbamate,
2-propoxy-2-n-propyl-1,3-benzodioxol-4-yl N-methylcarbamate,
2-methoxy-1,3-benzodioxol-4-yl N,N-dimethylcarbamate,
2-methoxy-2-methyl-1,3-benzodioxol-4-yl N,N-dimethylcarbamate,
2-methoxy-2-ethyl-1,3-benzodioxol-4-yl N,N-dimethylcarbamate,
2-methoxy-2-n-propyl-1,3-benzodioxol-4-yl N,N-dimethylcarbamate,
2-methoxy-2-isopropyl-1,3-benzodioxol-4-yl N,N-dimethylcarbamate,
2,2-dimethoxy-1,3-benzodioxol-4-yl N,N-dimethylcarbamate,
2-ethoxy-1,3-benzodioxol-4-yl N,N-dimethylcarbamate,
2-ethoxy-2-methyl-1,3-benzodioxol-4-yl N,N-dimethylcarbamate,
2-ethoxy-2-ethyl-1,3-benzodioxol-4-yl N,N-dimethylcarbamate,
2-ethoxy-2-propyl-1,3-benzodioxol-4-yl N,N-dimethylcarbamate,
2-ethoxy-2-isopropyl-1,3-benzodioxol-4-yl N,N-dimethylcarbamate, and
2-ethoxy-2-chloromethyl-1,3-benzodioxol-4-yl N,N-dimethylcarbamate.

In another aspect, this invention provides a process for the preparation of a compound of formula I, wherein $R^3$ represents hydrogen or a substituted or unsubstituted alkyl, alkenyl or alkynyl group, in which a 4-hydroxybenzodioxole of the general formula:

(II)

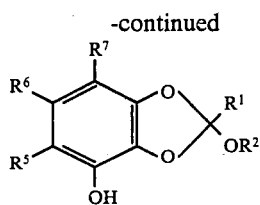

(wherein $R^1$, $R^2$, $R^5$, $R^6$ and $R^7$ are as defined hereinbefore) is reacted with a substituted carbamoyl chloride of formula $R^3R^4NCOCl$ (wherein $R^3$ represents hydrogen or a substituted or unsubstituted alkyl, alkenyl or alkynyl group and $R^4$ as defined hereinbefore) to give the corresponding compound of general formula I.

The reaction is usually carried out from 0° to 150° C, preferably in the presence of an equimolar amount of inorganic or tertiary organic base (e.g. sodium carbonate or preferably potassium carbonate) and preferably also in an inert solvent, e.g. pyriding (which can serve as the base and solvent) or acetone.

In a further aspect, this invention provides a process for the preparation of a compound of formula I wherein $R^3$ represents hydrogen, in which a 4-hydroxybenzodioxole of general formula II as defined hereinbefore is reacted with an isocyanate of formula $R^4NCO$ (wherein $R^4$ is as defined hereinbefore) to give the corresponding compound of general formula I.

This reaction is normally carried out at a temperature in the range 0° to 150° C, for example at ambient temperature, at a pressure of 0.5-10 atmospheres, preferably at 1-1.1 atmospheres, in an organic solvent, e.g. acetone, ether, dimethylformamide or a hydrocarbon (e.g. toluene), and preferably in the presence of a catalyst (usually a tertiary amine, e.g. triethylamine or pyridine, or an organotin compound e.g. dibutyltin diacetate). Where $R^4$ is methyl, the reaction is usually carried out in a vessel at 1-1.1 atmospheres and at a temperature in the range 0° to 60° C because of the boiling point of methyl isocyanate.

In a yet further aspect, this invention provides a process for the preparation of a compound of formula I wherein $R^3$ represents an alkanoyl group or a benzoyl group, in which a compound of formula I wherein $R^3$ represents hydrogen is acylated by reaction with an appropriate acylating agent.

The acylation is usually carried out from 0° to 150° C, e.g. in an inert solvent. The acylating agent may be an alkanoyl or benzoyl halide of formula $R^3X$ in which $R^3$ represents alkanoyl or benzoyl and X represents a haloen (usually chlorine) atom.

In a yet further aspect, this invention provides a process for the preparation of a compound of formula I, in which a 1,3-benzodioxol-4-yl chloroformate of the general formula:

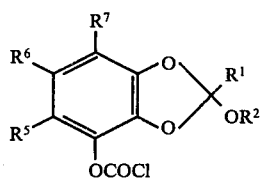

(III)

(wherein $R^1$, $R^2$, $R^5$, $R^6$ and $R^7$ are as defined hereinbefore) is reacted with an amine or amide of general formula $R^3R^4NH$ (wherein $R^3$ and $R^4$ are as defined hereinbefore) to give the corresponding compond of general formula I.

The reaction is usually carried out from 0° to 150° C, e.g. in an inert solvent (e.g. hydrocarbon or ether), and preferably in the presence of an equimolar amount of an inorganic base (e.g. sodium carbonate) or organic base (which may be an excess of the reacting amine or may for example be a tertiary amine such as triethylamine).

The 4-hydroxybenzodioxoles of general formula II and the 1,3-benzodioxol-4-yl chloroformates of general formula III are themselves novel compounds, and this invention provides them per se.

The 4-hydroxybenzodioxoles of general formula II may be prepared by a process in which a trihydroxybenzene of the general formula:

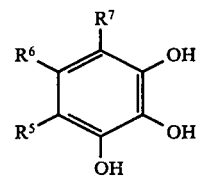

(IV)

(wherein $R^5$, $R^6$ and $R^7$ are as defined hereinbefore) is reacted with an ortho-ester of formula $R^1C(OR^2)_3$ (wherein $R^1$ and $R^2$ are as defined hereinbefore) to give the corresponding compound of general formula II.

The reaction is conveniently effected in a solvent which is inert under the reaction conditions, for example an aromatic hydrocarbon such as xylene or toluene, a halogenated hydrocarbon, for example 1,2-dichloroethane, chloroform or chlorobenzene, or an ether, for example di-isopropyl ether or dioxan. The temperature employed is preferably from 50° to 150° C, and more preferably from 80° to 120° C.

The 1,3-benzodioxol-4-yl chloroformates of general formula III may be prepared by reacting a 4-hydroxybenzodioxole of general formula II or a salt thereof with phosgene to give the corresponding chloroformate. This reaction is usually carried out at a temperature in the range 0° to 150° C, preferably in a hydrocarbon solvent and preferably also in the presence of an equimolar amount of a weak tertiary organic base, for example dimethylaniline.

The benzodioxol-4-yl carbamates of general formula I are pesticidally-active, possessing insecticidal activity inter alia against ants, houseflies, carpet beetles, carpet moths, mosquitos and fleas and especially against cockroaches, ticks and blowfly larvae. They act as contact insecticides, and possess systemic activity in addition. They may therefore be of use in the treatment of surfaces, crops, or animals which are infested or liable to infestation by such pests, and may especially be of use in the control of public health pests in, for example, hospitals and restaurants. They are of surprisingly low mammalian toxicity.

Before the compounds of this invention are so used, however, they are preferably formulated into an appropriate pesticidal composition.

In another aspect thereofore this invention provides a pesticidal composition comprising one or more benzodioxol-4-yl carbamates of general formula I in association with a suitable carrier or diluent and/or a surface active agent.

The benzodioxol-4-carbamates of general formula I are water insoluble, and may be formulated into an appropriate composition by any of the methods commonly employed for insoluble compounds.

For example, the compounds of formula I may be dissolved in a water immiscible solvent, for example a high boiling hydrocarbon, as a carrier, suitably containing dissolved emulsifying agents so that the composition acts as a self-emulsifiable oil on addition to water.

The compounds of formula I may alternatively be admixed with a surface active agent with or without a solid carrier to form a wettable powder which is soluble or dispersible in water, or may be mixed solely with a solid carrier to form a solid product.

Solid carriers in which the compounds of formula I may be incorporated include clays, sands, talc, mica or solid fertilizers, such products either comprising dust or larger particle size materials.

The surface active agents used may be anionic compounds such as soaps, fatty sulphate esters such as dodecyl sodium sulfate, octadecyl sodium sulphates or cetyl sodium sulphate, fatty aromatic sulphonates such as alkyl benzene sulphonates or butyl naphthalene sulphonate, more complex fatty sulphonates such as the amide condensation products of oleic acid and N-methyl taurine, or the sodium sulphonate of dioctyl succinate.

The surface active agents may alternatively be non-ionic surface active agents such as the condensation products of fatty acids, fatty alcohols or fatty substituted phenols with ethylene oxide, or fatty esters and ethers of sugars or polyhydric alcohols, or the products obtained from the latter by condensation with ethylene oxide, or block copolymers of ethylene oxide and propylene oxide.

The surface active agents may alternatively be cationic agents such as cetyl trimethylammonium bromide.

The pesticidal composition may be presented in the form of an aerosol composition, suitably employing a cosolvent and a surface active agent, in addition to the propellant, which is suitably a polyhalogenated alkane such as dichlorodifluoromethane.

The compositions of the present invention preferably contain from 0.5 to 99.5% by weight of the compound(s) of formula I. A more preferred content thereof is from 20 to 80% by weight.

The pesticidal compositions according to the present invention may contain in addition to the compounds of general formula I other pesticides, and particularly other insecticides, bactericides or fungicides, and/or synergists. Particularly preferred are the compositions of the present invention which also contain one or more other active insecticides and/or synergists. Suitable insecticides for use in the compositions of the present invention include carbamates, for example carbaryl, propoxur, aldicarb, carbofuran, 3,3-dimethyl-1-methylthio-2-butanone O-methylcarboyloxime, methomyl or bendiocarb, organocphosphorus compounds, for example dimethoate, terbufos, phorate, disulfoton, acephate, diazinon, dichlorvos or chlorpyrifos, organochlorine compounds, such as BHC or natural or synthetic pyrethrins, for example pyrethrin I and II, cinerin I and II, resmethrin and allethrin. Suitable synergists include piperonyl butoxide, piprotal, sesamex and sesamin.

If desired, the compositions of this invention may be employed to treat seeds to protect them from insect attack. Thus, the seeds may either be intimately admixed with a composition of this invention pre-planting, or else the seeds may be coated, conveniently by pelletisation, with such a composition.

In their various applications the compounds of the invention may be used at various rates; thus for example for the control of pests on plants the compounds are suitably applied at a rate of about 0.25–16 ounces per acre (17–1120g per hectare) and preferably 0.5–4 ounces per acre (35–280g per hectare); for the treatment of animals for the control of ticks, the animal is suitably dipped in or sprayed with a solution containing 30–300 parts per million of the active compound; for the treatment of seeds, the seed is suitablily treated with from 0.1 to 28g (more preferably 0.25 to 10g) of the compound(s) of the invention per kilgram of seed; and for the treatment of surfaces for the control of insects, e.g. public health pests, the compound(s) are preferably applied at a rate of from 10 to 500 mg/m², and more preferably at a rate of from 50 to 200 mg/m².

The following Examples are now given,, though only by way of illustration, to show details of the preparation and use of compounds of the present invention.

EXAMPLE 1

A mixture of pyrogallol (14.5g) and triethyl orthoacetate (18.5g) in xylene (75 ml) was heated at approximately 120° C so as to distil off the ethanol formed by the condensation of the reactants.. After the theoretical quantity of ethanol had been collected, the reaction mixture was cooled, washed with water (three times) and dried over sodium sulphate. The volume was then reduced to about 20 ml by distilling off the bulk of the solvent under reduced pressure, and to the concentrated solution of 4-hydroxy-2-ethoxy-2-methyl-1,3-benzodioxole was added methyl isocyanate (8 ml) and triethylamine (2 drops). The mixture was kept at room temperature for 40 minutes and the product filtered off, washed with xylene and then with petroleum (bp 40° C) and dried to give 2-ethoxy-2-methyl-1,3-benzodioxol-4-yl methylcarbamate (16.0g, 55% yield over two stages), melting point 97°–98.5° C.

Analysis: Found: C, 56.74; H, 6.06; N, 5.75%.
$C_{12}H_{15}NO_5$ requires: C, 56.91; H, 5.97; N, 5.53%.

EXAMPLE 2

2-Ethoxy-2-methyl-4-hydroxy-1,3-benzodioxole, prepared as in Example 1, (10g) was dissolved in dry acetone (100 ml). Dimethylcarbamoylchloride (8g) and potassium carbonate (12g) were added and the mixture stirred and heated under reflux for six hours. The mixture was then filtered and the solvent evaporated from the filtrate under reduced pressure. Distillation of the residue gave 2-ethoxy-2-methyl-1,3-benzodioxol-4-yl dimethylcarbamate (9.5g, 77% yield), boiling oint 120°–124° C/0.3 mmHg.

Analysis: Found: C, 58.27; H, 6.71; N, 5.16%.
$C_{13}H_{17}NO_5$ requires: C, 58.42; H, 6.41; N, 5.24%.

EXAMPLE 3

A mixture of pyrogallol (25 parts), trimethyl orthoformate (32 parts) and 1,2-dichloroethane (250 parts) was heated with continuous distillation of the solvent for 4 hours. The volume of solvent was kept constant by simultaneous addition of dichloroethane. The mixture was then washed three times with water and dried over sodium sulphate. Removal of the solvent under reduced pressure and distillation of the residue gave 4-hydroxy-2-methoxy-1,3-benzodioxole, boiling point 104°–105° C/1 mmHg.

EXAMPLES 4–19

The following methylcarbamates were prepared by a method analogous to that described in Example 1 by reacting the appropriate substituted 4-hydroxy-1,3-benodioxole (prepared from pyrogallol and the appropriate ortho ester) with methyl isocyanate:

2-methoxy-1,3-benzodioxol-4-yl N-methylcarbamate, mp 115°–7°;
2-methoxy-2-methyl-1,3-benzodioxol-4-yl N-methylcarbamate, mp 115°–8°;
2-methoxy-2-ethyl-1,3-benzodioxol-4-yl N-methylcarbamate, mp 57°–60°;
2-methoxy-2-n-propyl-1,3-benzodioxol-4-yl N-methylcarbamate, 52°–54°;
2-methoxy-2-isopropyl-1,3-benzodioxol-4-yl N-methylcarbamate, mp 73°–74°;
2-methoxy-2-chloromethyl-1,3-benzodioxol-4-yl N-methylcarbamate, mp 101°–102°;
2-methoxy-2-phenyl-1,3-benzodioxol-4-yl N-methylcarbamate; mp 121°–125°;
2,2-dimethoxy-1,3-benzodioxol-4-yl N-methylcarbamate, mp 41°–44°;
2-ethoxy-1,3-benzodioxol-4-yl N-methylcarbamate, mp 81°–83°;
2-ethoxy-2-ethyl-1,3-benzodioxol-4-yl N-methylcarbamate, mp 67°–69°;
2-ethoxy-2-n-propyl-1,3-benzodioxol-4-yl N-methylcarbamate, mp 75°–77°;
2-ethoxy-2-isopropyl-1,3-benzodioxol-4-yl N-methylcarbamate, mp 96°–97°;
2-ethoxy-2-chloromethyl-1,3-benzodioxol-4-yl N-methylcarbamate, mp 105°–107°;
2-ethoxy-2-ethylthiomethyl-1,3-benzodioxol-4-yl N-methylcarbamate, mp 68°–70°;
2-propoxy-2-ethyl-1,3-benzodioxol-4-yl N-methylcarbamate, mp 84°–84°; and
2-propoxy-2-n-propyl-1,3-benzodioxol-4-yl N-methylcarbamate, mp 83°–89°.

EXAMPLES 20–30

The following dimethylcarbamates were prepared by a method analogous to that described in Example 2 by reacting the appropriate substituted 4-hydroxy-1,3-benzodioxole (prepared from pyrogallol and the appropriate ortho ester) with dimethylcarbamoyl chloride:

2-methoxy-1,3-benzodioxol-4-yl N,N-dimethylcarbamate, bp 112°–114°/0.4 mmHg;
2-methoxy-2-methyl-1,3-benzodioxol-4-yl N,N-dimethylcarbamate, bp 110°–5°/0.3 mmHg;
2-methoxy-2-ethyl-1,3-benzodioxol-4-yl N,N-dimethylcarbamate, bp 106°/0.1 mmHg;
2-methoxy-2-n-propyl-1,3-benzodioxol-4-yl N,N-dimethylcarbamate, bp 130°–3°/0.4 mmHg;
2-methoxy-2-isopropyl-1,3-benzodioxol-4-yl N,N-dimethylcarbamate, bp 123°–5°/0.25 mmHg;
2,2-dimethoxy-1,3-benzodioxol-4-yl N,N-dimethylcarbamae, colourless liquid, decomposes on distillation,
2-ethoxy-1,3-benzodioxol-4-yl N,N-dimethylcarbamate, bp 114°–119°/0.12 mmHg;
2-ethoxy-2-ethyl-1,3-benzodioxol-4-yl N,N-dimethylcarbamate, bp 120°–4°/0.1 mmHg;
2-ethoxy-2-n-propyl-1,3-benzodioxol-4-yl N,N-dimethylcarbamate, bp 128°–9°/0.4 mmHg;
2-ethoxy-2-isopropyl-1,3-benzodioxol-4-yl N,N-dimethylcarbamate, bp 124°–5°/0.3 mmHg;
2-ethoxy-2-chloromethyl-1,3-benzodioxol-4-yl N,N-dimethylcarbamate, mp 70°–72° C.

EXAMPLE 31

1 ml aliquots of acetone solutions of the compounds listed below were applied to the inside of glass jars at concentrations such as to produce deposits equivalent to 500, 150, 50, 15, 5 and 1.5 mg/m². When the solvent had evaporated off, the treated surfaces were infested with fifth instar nymphs of the German cockroach, *Blattella germanicia*, and the jars closed with a screw cap perforated for ventilation. They were then kept at 20° C for seven days and the percentage mortality of the insects then noted. The $LD_{50}$ for each compound was then calculated and is set out below. In the table, 6 indicates an $LD_{50}$ of less than 1.5 mg/m², 5 from 1.5 to 5 mg/m², 4 from 5 to 15 mg/m², 3 from 15 to 50 mg/m², 2 from 50 to 150 mg/m² and 1 from 150 to 500 mg/m².

| Compound | $LD_{50}$ code |
| --- | --- |
| 2-methoxy-1,3-benzodioxol-4-yl N-methylcarbamate | 6 |
| 2-methoxy-2-methyl-1,3-benzodioxol-4-yl N-methylcarbamate | 6 |
| 2-methoxy-2-ethyl-1,3-benzodioxol-4-yl N-methylcarbamate | 5 |
| 2-methoxy-2-isopropyl-1,3-benzodioxol-4-yl N-methylcarbamate | 3 |
| 2-methoxy-2-n-propyl-1,3-benzodioxol-4-yl N-methylcarbamate | 6 |
| 2,2-dimethoxy-1,3-benzodioxol-4-yl N-methylcarbamate | 5 |
| 2-ethoxy-1,3-benzodioxol-4-yl N-methylcarbamate | 5 |
| 2-ethoxy-2-methyl-1,3-benzodioxol-4-yl N-methylcarbamate | 5 |
| 2-ethoxy-2-ethyl-1,3-benzodioxol-4-yl N-methylcarbamate | 4 |
| 2-methoxy-2-methyl-1,3-benzodioxol-4-yl N,N-dimethylcarbamate | 4 |
| 2-methoxy-2-ethyl-1,3-benzodioxol-4-yl N,N-dimethylcarbamate | 3 |
| 2-methoxy-2-isopropyl-1,3-benzodioxol-4-yl N,N-dimethylcarbamate | 3 |
| 2-methoxy-2-n-propyl-1,3-benzodioxol-4-yl N,N-dimethylcarbamate | 4 |
| 2-ethoxy-1,3-benzodioxol-4-yl N,N-dimethylcarbamate | 3 |
| 2-ethoxy-2-methyl-1,3-benzodioxol-4-yl N,N-dimethylcarbamate | 3 |
| 2-ethoxy-2-ethyl-1,3-benzodioxol-4-yl N,N-dimethylcarbamate | 4 |
| 2-ethoxy-2-isopropyl-1,3-benzodioxol-4-yl N,N-dimethylcarbamate | 3 |

EXAMPLE 32

A wettable powder was prepared by mixing, grinding and micronising the following:

2-methoxy-2-methyl-1,3-benzodioxol-4-yl-N-methylcarbamate: 50%
Reax 45L (combined wetting and dispersing agent based on lignin sulphonate salt): 5%
China clay: 45%

EXAMPLE 33

A wettable powder was prepared by mixing, grinding and micronising the following:

2-methoxy-1,3-benzodioxol-4-yl N-methylcarbamate: 25%
Reax 45L (combined wetting and dispersing agent based on lignin sulphonate salt): 5%
China clay: 70%

EXAMPLE 34

A wettable powder was prepared by mixing, grinding and micronising the following:

2-methoxy-1,3-benzodioxol-4-yl N-methylcarbamate: 65%
Arkopon T (sodium N-methyltauride) 5%
Neosyl (precipitated silica): 30%

I claim:

1. The benzodioxol-4-yl carbamates of the formula $$\text{(I)}$$

wherein $R^1$ represents hydrogen, an alkyl group of 1 to 6 carbon atoms which may be unsubstituted or substituted by halogen, alkylthio or by alkoxy, a phenyl group which may be unsubstituted or substituted by haloen, alkoxy or by alkyl, or a group —$OR^2$ where $R^2$ is as defined hereinafter;

$R^2$ represents an alkyl group of 1 to 6 carbon atoms which may be unsubstituted or substituted by halogen or by alkoxy;

$R^3$ represents hydrogen or an alkyl, alkenyl or alkynyl group of not more than 4 carbon atoms which may be unsubstituted or substituted by halogen or by alkoxy, or an alkanoyl group of 2 to 10 carbon atoms; and $R^4$ represents an alkyl, alkenyl or alkynyl group of not more than 4 carbon atoms which may be unsubstituted or substituted by halogen or by alkoxy.

2. The benzodioxol-4-yl carbamates according to claim 1 wherein $R^1$ represents hydrogen, alkyl of 1 to 6 carbon atoms which may be unsubstituted or substituted by a halogen atom or by an alkylthio group, alkoxy of 1 to 6 carbon atoms, or phenyl.

3. The benzodioxol-4-yl carbamates according to claim 1 wherein $R^2$ represents unsubstituted alkyl of 1 to 6 carbon atoms.

4. The benzodioxol-4-yl carbamates according to claim 1 wherein $R^3$ represents hydrogen or unsubstituted alkyl of 1 to 4 carbon atoms and $R^4$ represents unsubstituted alkyl of 1 to 4 carbon atoms.

5. The benzodioxol-4-yl carbamates according to claim 1 wherein $R^1$ represents hydrogen, alkyl of 1 to 6 carbon atoms, which may be unsubstituted or substituted by a haloen atom or by an alkylthio group, alkoxy of 1 to 6 carbon atoms, or phenyl;

$R^2$ represents unsubstituted alkyl of 1 to 6 carbon atoms;

$R^3$ represents hydrogen or unsubstituted alkyl or 1 to 4 carbon atoms; and $R^4$ represents unsubstituted alkyl of 1 to 4 carbon atoms.

6. A benzodioxol-4-yl carbamate selected from:
2-methoxy-1,3-benzoidoxol-4-yl N-methylcarbamate,
2-methoxy-2-methyl-1, 3-benzodioxol-4-yl N-methylcarbamate,
2-methoxy-2-ethyl-1,3-benzodioxol-4-yl N-methylcarbamate,
2-methoxy-2n-propyl-1,3-benzodioxol-4-yl N-methylcarbamate,
2-methoxy-2-isopropyl-1,3-benzodioxol-4-yl N-methylcarbamate,
2-methoxy-2-chloromethyl-1,3-benzodioxol-4-yl N-methylcarbamate,
2-methoxy-2-phenyl-1,3-benzodioxol-4-yl N-methylcarbamate,
2,2-dimethoxy-1,3-benzodioxol-4-yl N-methylcarbamate,
2-ethoxy-1,3-benzodioxol-4-yl N-methylcarbamate,
2-ethoxy-2-methyl-1,3-benzodioxol-4-yl N-methylcarbamate,
2-ethoxy-2-ethyl-1,3-benzodioxol-4-yl N-methylcarbamate,
2-ethoxy-2-n-propyl-1,3-benzodioxol-4-yl N-methylcarbamate,
2-ethoxy-2-isopropyl-1,3-benzodioxol-4-yl N-methylcarbamate,
2-ethoxy-2-chloromethyl-1,3-benzodioxol-4-yl N-methylcarbamate,
2-ethoxy-2-ethylthiomethyl-1,3-benzodioxol N-methylcarbamate,
2-propoxy-2-ethyl-1,3-benzodioxol-4-yl N-methylcarbamate,
2-propoxy-2-n-propyl-1,3-benzodioxol-4-yl N-methylcarbamate,
2-methoxy-1,3-benzodioxol-4-yl N,N-dimethylcarbamate,
2-methoxy-2-methyl-1,3-benzodioxol-4-yl N,N-dimethylcarbamate,
2-methoxy-2-ethyl-1,3-benzodioxol-4-yl N,N-dimethylcarbamate,
2-methoxy-2-n-propyl-1,3-benzodioxol-4-yl N,N-dimethylcarbamate,
2-methoxy-2-isopropyl-1,3-benzodioxol-4-yl N,N-dimethylcarbamate,
2,2-dimethoxy-1,3-benzodioxol-4-yl N,N-dimethylcarbamate,
2-ethoxy-1,3-benzodioxol-4-yl N,N-dimethylcarbamate,
2-ethoxy-2-methyl-1,3-benzodioxol-4-yl N,N-dimethylcarbamate,
2-ethoxy-2-ethyl-1,3-benzodioxol-4-yl N,N-dimethylcarbamate,
2-ethoxy-2-propyl-1,3-benzodioxol-4-yl N,N-dimethylcarbamate,
2-ethoxy-2-isopropyl-1,3-benzodioxol-4-yl N,N-dimethylcarbamate, and 2-ethoxy-2-chloromethyl-1,3-benzodioxol-4-yl N,N-dimethylcarbamate.

7. A pesticidal composition comprising one or more benzodioxol-4-yl carbamates as claimed in claim 1 in association with a suitable carrier or diluent and/or a surface active agent.

8. A method of combating insects which comprises applying to a locus either infested with or liable to infestation by said insects an insecticidally-effective amount of one or more benzodioxol-4-yl carbamates as claimed in claim 1.

9. The compounds of the formula (II) 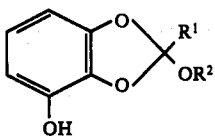

wherein R[1] represents hydrogen, an alkyl group of 1 to 6 carbon atoms which may be unsubstituted or substituted by halogen, alkylthio or by alkoxy, a phenyl group which may be unsubstituted or substituted by haloen, alkoxy or by alkyl, or a group —OR[2] where R[2] is as defined herinafter; and R[2] represents an alkyl group of 1 to 6 carbon atoms which may be unsubstituted or substituted by halogen or by alkoxy.

10. The compounds according to claim 9 wherein R[1] represents hydrogen, alkyl of 1 to 6 carbon atoms, which may be unsubstituted or substituted by a halogen atom or by an alkylthio group, alkoxy of 1 to 6 carbon atoms, or phenyl; and R[2] represents unsubstituted alkyl of 1 to 6 carbon atoms.

11. The compounds of the formula (III) 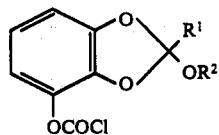

wherein R[1] represents hydrogen, an alkyl group of 1 to 6 carbon atoms which may be unsubstituted or substituted by halogen, alkylthio or by alkoxy, a phenyl group which may be unsubstituted or substituted by halogen, alkoxy or by alkyl, or a group —OR[2] where R[2] is as defined hereinafter;

R[2] represents an alkyl group of 1 to 6 carbon atoms which may be unsubstituted or substituted by halogen or by alkoxy.

12. The compounds according to claim 11 wherein R[1] represents hydrogen, alkyl of 1 to 6 carbon atoms, which may be unsubstituted or substituted by a halogen atom or by an alkylthio group, alkoxy of 1 to 6 carbon atoms, or phenyl; and R[2] represents unsubstituted alkyl of 1 to 6 carbon atoms.

* * * * *